United States Patent [19]

Anderson et al.

[11] 3,932,608

[45] Jan. 13, 1976

[54] FOOD COMPOSITION

[75] Inventors: Ray H. Anderson, Osseo; Albert L. Saari, Minneapolis, both of Minn.

[73] Assignee: General Mills, Inc., Minneapolis, Minn.

[22] Filed: Aug. 30, 1971

[21] Appl. No.: 176,276

[52] U.S. Cl. .................. 424/54; 424/48; 426/3; 426/190; 426/208; 426/212; 426/213; 426/214; 426/218
[51] Int. Cl.² ................ A61K 5/00; A61K 7/16
[58] Field of Search ............ 424/54, 199, 48; 426/3, 426/190, 208, 212, 213, 214, 218

[56] References Cited
UNITED STATES PATENTS 3,231,388   1/1966   White ..................................... 99/92

*Primary Examiner*—Shep K. Rose
*Attorney, Agent, or Firm*—Gene O. Enockson; Norman P. Friederichs; Anthony A. Juettner

[57] ABSTRACT

A food composition is disclosed which contains an amino acid phosphate, namely, an alkali metal amino acid phosphate or an alkaline earth metal amino acid phosphate. The amino acid phosphate serves as a cariostatic agent and as an agent for nutritional fortification.

7 Claims, No Drawings

FOOD COMPOSITION

The present invention relates to a food composition and more particularly to a food product including a cariostatic agent and nurtitional fortification.

In the past various types of cariostatic compositions have been proposed. For example, materials such as stannous fluoride, calcium carbonate and sodium hydrogen phosphate have been proposed for reducing dental caries. Cariostatic agents may be applied topically to the teeth, included in dentifrice compositions, or included in foods. The present invention relates to an amino acid phosphate which is particularly suitable for use in food products. The present cariostatic composition is not toxic and in fact is nutritious providing amino acid fortification of the food product. Moreover, the present cariostatic composition is highly compatible with food products and does not adversely affect the taste of the food to which it is added.

The cariostatic composition used in the present invention may be prepared by reacting an amino acid in the free base form with phosphoric acid to form an amino acid phosphate. The amino acid phosphate may be then reacted with a base or basic salt of an alkali metal or an alkaline earth metal to form an alkaline amino acid phosphate. In some instances the cariostatic agent may be prepared by reacting the free base amino acid directly with an alkali metal phosphate or an alkaline earth metal phosphate. The term "alkaline amino acid phosphate" as used herein includes alkali metal amino acid phosphates, alkaline earth metal amino acid phosphates and their diphosphates.

Any amino acid may be used in preparing the cariostatic composition of the present invention providing the amino acid will react to form the alkaline amino acid phosphate. However, the amino acid is preferably an essential amino acid for purposes of nutrition. The amino acids used to prepare the cariostatic composition typically include lysine, ornithine, arginine, tryptophan, phenyl alanine, leucine, isoleucine, threonine, methionine, valine, hydroxyproline and glycine. The preferred amino acid is L-lysine. The amino acid is preferably in the free base form when used to prepare the cariostatic composition. Certain of the free base amino acids, typically L-lysine, are unstable and therefore may be produced from the hydrochloride immediately prior to use in producing the cariostatic composition. The free base amino acid may be prepared by passing a water solution of the amino acid hydrochloride through a resin column in the OH$^-$ ionic form. Other amino acids may be obtained commercially in the free base form. The free base amino acid may be reacted with a phosphoric acid such as orthophosphoric acid in a molar weight ratio of from 1:1 to 1:2 to produce the amino acid phosphate. For nutritional purposes the 1:1 ratio (i.e. monophosphate) is preferred whereas, for cariostatic purposes, the 1:2 (i.e. diphosphate) ratio is preferred. The amino acid phosphate as a water solution may be reacted with the alkali metal compound or the alkaline earth metal compound. These compounds may be a base or basic salt. In other words the alkali metal compound may be an oxide or a hydroxide of sodium or potassium. The alkali metal compound may be a basic salt such as a carbonate or bicarbonate of sodium or potassium. The alkaline earth metal compound may be an oxide, hydroxide, carbonate or bicarbonate such as of calcium or magnesium. The alkali metal compound or alkaline earth metal compound may be added to the amino acid phosphate solution in the form of a dry product such as pellets or flakes or in the form of an aqueous solution.

The amino acid phosphate, in the case of basic amino acids, may be reacted with the alkali metal compound or alkaline earth metal compound in a ratio of one mole of amino acid phosphate to between one and two equivalent weights of the alkali metal compound or alkaline earth metal compound. In the case of the phosphates of neutral amino acids the ratio may be one mole of amino acid phosphate to one equivalent weight of alkali metal compound or alkaline earth metal compound.

The alkaline amino acid phosphate solution may be applied as is to the food composition or may be concentrated by precipitation and/or evaporation. The alkaline amino acid phosphate may be precipitated at room temperature with a water-miscible organic solvent such as methanol, ethanol, acetone or mixtures of such solvents. The precipitate may be washed with the water-miscible solvent and dried. The alkaline amino acid phosphate solution, alternatively, may be concentrated by evaporation, such as vacuum drying, to a concentration of about 40 to 50% solids.

The food composition of the present invention may be any cereal or sugar containing food product such as bread, breakfast cereal (either presweetened or unsweetened), various baked goods (i.e. cakes, pies, cookies and the like), casseroles (i.e. noodles and the like), candy, chewing gum and soft drinks. For cariostatic purposes the alkaline amino acid phosphate will generally be present in an amount of at least 0.05% phosphorous based on the total weight of the food product. For economic reasons the alkaline amino acid phosphate will rarely be present in an amount greater than 0.2% phosphorous based on the total weight of the food product and the preferred level is 0.1%. For nutritional purposes, i.e. amino acid fortification of protein containing food products, the alkaline amino acid phosphate is prepared from the desired essential amino acid and is present in a range of 0.5% to 3.0%, preferably 1% to 2% based on the total weight of the protein present. The alkaline amino acid phosphate may be combined with the food product in any of various ways such as spraying a solution onto the surface of the food product, mixing a dry form with the dry finished food product, or mixing with the other ingredients prior to baking.

The following examples are for purposes of illustrating the present invention and are not intended to be limiting.

EXAMPLE I

An alkaline amino acid phosphate was prepared for use in the present invention by passing a 10% (by weight) solution of L-lysine hydrochloride through a resin column to produce free base lysine. The resin column was 20 inches in height and was an IR-410 (Amberlite) in the OH$^-$ ionic form. The solution was passed through the column at the rate of 2 to 3 milliliters per square centimeter of column per minute. The free base lysine was eluted with water. One molar part of the free base lysine was added to a flask containing one molar part of orthophosphoric acid. The term "part" as used herein will mean "part by weight" unless otherwise indicated. One molar part of orthophosphoric acid was added to the aqueous solution of lysine phosphate thereby producing lysine diphosphate. One molar part of sodium hydroxide pellets was added to the lysine diphosphate. Then one molar part of potassium hydroxide pellets was added to the solution with thorough mixing. The resulting solution was evaporated to approximately 45% solids in a vacuum using a rotary evaporator. The concentrated solution of sodium potassium lysine diphosphate was found to be stable at room temperature.

EXAMPLE II

An alkaline amino acid phosphate (potassium lysine phosphate), suitable for use in the present invention, was prepared by passing a 10% (by weight) L-lysine hydrochloride solution in an amount of 455 grams through the resin column as described in Example I. The resulting free base lysine was added to 3470 ml. of an aqueous solution containing 345 g. of $KH_2PO_4$. One half of the resulting solution was evaporated to about 700 ml. and then 750 ml. of methanol were added. The mixture was cooled to 5°C. and the potassium lysine phosphate precipitated. The precipitate was collected by filtration and air dried.

EXAMPLE III

An alkaline amino acid phosphate (potassium lysine diphosphate) was prepared from the remaining solution of Example II by adding to such solution 85 milliliters of an 85% $H_3PO_4$ solution. The resulting solution was evaporated to 750 milliliters and 750 milliliters of methanol were added. The mixture was cooled to 5°C. and the potassuim lysine diphosphate precipitated. The precipitate was collected by filtration.

EXAMPLE IV

Sodium lysine diphosphate was prepared by passing 300 millimoles of L-lysine hydrochloride through a resin column to produce free base lysine. The resin used was Rexyn AGI in the OH⁻ form. To the free base L-lysine was added 300 millimoles of sodium dihydrogen phosphate. Then 300 millimoles of orthophosphoric acid were added with thorough stirring. The resulting solution was evaporated in a vacuum until a milky appearance was acquired and then cooled to 5°C. The material was filtered and a tacky crystalline material was obtained and air dried. The material was identified as Na Lysine $H_5(PO_4)_2$.

EXAMPLE V

An alkaline amino acid phosphate, K $LysH_5(PO_4)_2$.$LysH_6(PO_4)_2$, was prepared by adding 2.5 moles of free base lysine to 2.5 moles of $H_3PO_4$. Then 2.5 moles of $H_3PO_4$ were added. The resulting solution was divided into two equal portions A and B. To Portion A was added 0.625 equivalent weights of $K_2CO_3$. The resulting solution was found to contain K $LysH_5 (PO_4)_2$.$LysH_6(PO_4)_2$.

EXAMPLE VI

An alkaline amino acid phosphate, K $LysH_4(PO_4)_2$, was prepared from Portion B by the addition of 2.5 equivalent weights of $K_2CO_3$ with thorough mixing.

EXAMPLE VII

An unsweetened breakfast cereal was prepared according to the present invention. A 40% aqueous solution of the sodium lysine diphosphate of Example IV was applied to the cornflakes in an enrober by spraying. Sufficient solution was applied to provide the flakes with an added phosphorous content of 0.08% by weight. The flavor of the corn flakes was not impaired.

EXAMPLE VIII

A sweetened breakfast ceral was prepared according to the present invention. A syrup was prepared including 436 grams sucrose, 91 grams corn syrup, 9 grams salt and 50 grams water. The syrup was heated to boiling and 1.24 grams of sodium lysine diphosphate was added and thoroughly mixed into the hot syrup. Appreciable browning occurred when the lysine phosphate was added to the hot syrup resulting in an attractive color and a good caramel flavor. The syrup was immediately poured onto 670 grams of corn flakes in a batch type enrober. The coated flakes were dried at 170°F. for about 30 minutes. The final moisture content was 4%.

EXAMPLE IX

White bread was prepared according to the present invention. A dry mixture was prepared including 84 parts flour, 0.25 part sodium lysine diphosphate, 5.2 parts sugar, 1.6 parts salt and 6.8 parts vegetable shortening. ABout 60 parts of warm water were combined with 1.8 parts fresh yeast and 0.4 part yeast food. The yeast suspension was added to the dry ingredients to form a dough. The dough was kneaded until developed. The dough was then held at 90°F. for 75 minutes for proofing. The dough was punched down and held at 90°F. for 25 minutes for proofing. The dough was cut into 600 gram units and formed into loaves. The formed loaves were held at 90°F. for 35 minutes for proofing and then baked at 420°F. for one hour. Control bread was identically prepared except that sodium lysine diphosphate was not added. In both instances the bread was sliced, dried at 150°F. and ground to pass through a No. 70 wire screen. Rat Group A (ten Cotton rats) was fed a diet including 1 part ground bread containing sodium lysine diphosphate and 2 parts standard cariogenic dietary material. The standard cariogenic dietary material included 32 parts oat groats, 32 parts whole milk powder and 2 parts liver powder. Rat Group B (10 Cotton rats) was fed a diet including 1 part ground control bread and 2 parts of the standard cariogenic dietary material. Both groups were fed for 28 days. Group A was found to have fewer caries than Group B. The caries considered were sulcal caries or in other words pit and fissure caries as measured on the first and second molars. The first molars in Group A received an average score of 6.6 per rat tooth and those in Group B received an average score of 8.9, basis number of caries. The first molars in Group A received an average score of 13.7 and those in Group B received an average score of 18.5, basis severity of caries. The second molars in Group A received an average score of 6.8 and those in Group B received an average score of 7.8, basis number of caries. The second molars in Group A received an average score of 14.5 and those in Group B received an average score of 16.3, basis severity of caries. Thus the results show a reduction in both number and severity of caries using the present food composition. The alkaline amino acid phosphate, when used in a diet for cariostatic purposes, is present in a cariostatic effective amount.

EXAMPLE X

Cream type fillings were prepared according to the present invention including approximately 27 to 30% fat, 15 to 20% protein concentrate and 45 to 50% confectioner's sugar. Various vitamins, minerals, flavor and coloring were added. Three grams of the sodium lysine diphosphate were added to 200 grams of the cream type filling. The sodium lysine diphosphate produced no noticeable effect on the physical properties or flavor of the filling. The filling was suitable for use with cookies or cakes.

EXAMPLE XI

The food composition was tested as a dietary supplement for lysine fortification on rats. The diet consisted of 12 parts wheat gluten, 69 parts corn starch and 8 parts vegetable shortening. Rat Group A was a control group and received the diet without added lysine. Rat GRoup B received the diet supplemented with 1% equivalent lysine based on weight of gluten. The lysine used with Group B was lysine hydrochloride. Rat Group C received the diet supplemented with NaK lysine diphosphate in the same lysine equivalent level as Group B. The effect of the supplement was determined as PER (Protein Efficiency Ratio). The PER was as follows:

| Group | Added Lysine | PER |
|-------|--------------|-----|
| A | No | 0.63 |
| B | Lysine hydrochloride | 0.91 |
| C | NaK lysine diphosphate | 1.98 |

The alkaline amino acid phosphate when used for amino acid fortification is present in a nutritionally effective amount.

The embodiments of the invention in which an exclusive property or privilege is claimed are defined as follows:

1. A cariogenic food product fortified nutritionally with a cariostatic effective amount of a member selected from the group consisting of an alkali metal lysine phosphate, an alkaline earth metal lysine phosphate and their diphosphates.

2. The food product of claim 1 wherein the amino acid phosphate is a member of the group consisting of sodium and potassium lysine phosphate.

3. The food product of claim 1 wherein said food product is candy.

4. The food product of claim 1 wherein said food product is chewing gum.

5. The food product of claim 1 wherein said food product is a soft drink.

6. The food product of claim 1 wherein said food product is a presweetened breakfast cereal, said cereal being sweetened by coating with a syrup and wherein said lysine phosphate or diphosphate is included in said syrup.

7. A cariogenic food product fortified nutritionally with a cariostatic effective amount of a member selected from the group consisting of an alkali metal lysine diphosphate said cariogenic food product being selected from the group consisting of cereals and sugars, said diphosphate being present in an amount of from 0.05 to 0.2% phosphorus based on the total weight of the food product, said diphosphate being used as a cariostatic agent.

* * * * *